(12) United States Patent
Liu et al.

(10) Patent No.: US 11,730,386 B2
(45) Date of Patent: Aug. 22, 2023

(54) ELECTRICAL IMPEDANCE TOMOGRAPHY WITH FDM-BASED DATA COMPRESSION

(71) Applicants: Shanghai Jiao Tong University, Shanghai (CN); National University of Singapore, Singapore (SG)

(72) Inventors: Boxiao Liu, Shanghai (CN); Yong Lian, Shanghai (CN); Lei Zeng, Singapore (SG); Chun Huat Heng, Singapore (SG)

(73) Assignees: Shanghai Jiao Tong University, Shanghai (CN); National University of Singapore, Singapore (SG)

( * ) Notice: Subject to any disclaimer, the term of this patent is extended or adjusted under 35 U.S.C. 154(b) by 857 days.

(21) Appl. No.: 16/678,960

(22) Filed: Nov. 8, 2019

(65) Prior Publication Data
US 2020/0146585 A1 May 14, 2020

(30) Foreign Application Priority Data
Nov. 9, 2018 (SG) .......................... 10201809972V

(51) Int. Cl.
*A61B 5/0536* (2021.01)
(52) U.S. Cl.
CPC ................................. *A61B 5/0536* (2013.01)
(58) Field of Classification Search
None
See application file for complete search history.

(56) References Cited

U.S. PATENT DOCUMENTS

| 4,895,163 | A | * | 1/1990 | Libke | ................... | A61B 5/4872 |
| | | | | | | 600/382 |
| 5,182,642 | A | * | 1/1993 | Gersdorff | ................. | H04N 7/54 |
| | | | | | | 375/240.18 |

(Continued)

OTHER PUBLICATIONS

S. Hong et al., "A 4.9mΩ-Sensitivity Mobile Electrical Impedance Tomography IC for Early Breast-Cancer Detection System," IEEE Journal of Solid-State Circuits, vol. 50, No. 1, pp. 245-257 (Jan. 2015).

(Continued)

*Primary Examiner* — Matthew Kremer
(74) *Attorney, Agent, or Firm* — Mei & Mark LLP; Manni Li

(57) ABSTRACT

An electrical impedance tomography system with frequency division multiplexing based data compression comprising electrodes, a connecting line, an electrical impedance tomography chip, a universal serial bus and a computer. The present invention realizes the proposed electrical impedance tomography system by innovative application of frequency division multiplexing technology, and has the advantages of low power consumption and improved hardware overheads. The architecture of the 13-channel electrical impedance tomography chip introduced in the embodiment of the present invention, which applies the frequency division multiplexing based data compression technology, has taped out using CMOS 0.13 micrometer process; the power consumption per channel turns out to be 118 microwatts and the area is 0.87 square millimeters, verifying the effectiveness of the present invention. The present invention can also be migrated to other applications of electrical impedance tomography.

3 Claims, 7 Drawing Sheets

(56) References Cited

U.S. PATENT DOCUMENTS

| | | | |
|---|---|---|---|
| 2006/0085049 A1* | 4/2006 | Cory | A61B 5/4041 |
| | | | 607/48 |
| 2013/0116577 A1* | 5/2013 | Yazicioglu | H01L 27/0811 |
| | | | 600/483 |
| 2016/0073908 A1* | 3/2016 | Khachaturian | G01K 7/42 |
| | | | 600/474 |
| 2018/0092560 A1* | 4/2018 | Holder | A61B 5/6884 |
| 2018/0132750 A1* | 5/2018 | Kalb | H03M 3/414 |

OTHER PUBLICATIONS

S. Hong et al., "A 10.4mW Electrical Impedance Tomography SoC for Portable Real-Time Lung Ventilation Monitoring System," IEEE Asian Solid-State Circuits Conference, Kaohsiung, Taiwan, No. 978-1-4799-4089-9/14, pp. 193-196 (Nov. 10-12, 2014).

M. Kim et al., "A 1.4-m$\Omega$-Sensitivity 94-dB Dynamic-Range Electrical Impedance Tomography SoC and 48-channel Hub-SoC for 3-D Lung Ventilation Monitoring System," IEEE Journal of Solid-State Circuits, vol. 52, No. 11, pp. 2829-2842 (Nov. 2017).

Liu, Boxiao et al., "A 13-channel 1.53-mW 11.28-mm$^2$ electrical impedance tomography SoC based on frequency division multiplexing for lung physiological imaging," IEEE Transactions on Biomedical Circuits and Systems, vol. 13, No. 5, pp. 938-949 (Oct. 2019).

Liu, Boxiao et al., "A 13-channel 1.53-mW 11.28-mm$^2$ electrical impedance tomography SoC based on frequency division multiplexing with 10x throughput reduction," 2019 IEEE International Solid-State Circuits Conference, 978-1-5386-8531-0/19, ISSCC 2019/Session 22/Physiological Monitoring/22.6, Digest of Technical Papers, pp. 370-372 (Feb. 20, 2019).

\* cited by examiner

ELECTRICAL IMPEDANCE TOMOGRAPHY WITH FDM-BASED DATA COMPRESSION

CROSS-REFERENCE TO RELATED APPLICATION

The subject application claims priority on Singaporean patent application no. 10201809972V filed on Nov. 9, 2018 in Singapore. The contents and subject matter of the Singaporean priority application is incorporated herein by reference.

TECHNICAL FIELD

The present invention relates to electronic technology and biomedical imaging, and in particular, an electrical impedance tomography system with frequency division multiplexing (FDM) based data compression technology.

BACKGROUND OF INVENTION

Traditional medical imaging technologies include electronic computed tomography, ultrasound, nuclear magnetic resonance, etc., which generally have problems such as large equipment size and high cost of use. Traditional medical imaging technologies are also harmful to health.

Electrical impedance tomography is a new type of medical imaging technique. Its principle is to apply a safe-intensity current to human body with a pair of surface electrode, and measure the voltage value on other electrodes, accordingly, reconstructing the electrical impedance value or the change in electrical impedance value of the internal structure of human body. Compared with traditional technology, electrical impedance tomography has the advantages of low cost, high safety, easy-to-carry equipment, and low requirement for the physical examination environment, making portable/wearable continuous monitoring possible.

At present, most electrical impedance tomography systems are based on time division multiplexing (TDM) or active electrodes. The circuit structure based on time division multiplexing lowers the area consumption, but is limited by the switching time between channels, and causes additional power consumption for the time division multiplexer (MUX). The active electrode system effectively eliminates the distortion from transmission through cables, but its redundant design will increase the area consumption of the whole system and thus raise the total cost. How to reduce chip area and power consumption, thereby increasing the integration of multiple channels and increasing the monitoring time is a key issue for the development of bioelectrical impedance tomography systems to portable or wearable.

The key problem to solve is how to reduce the chip area and power consumption in order to achieve multi-channel integration and increase the monitoring duration, if we want to develop portable or wearable electrical impedance tomography systems and devices.

SUMMARY OF THE INVENTION

The present invention provides an electrical impedance tomography system with frequency division multiplexing based data compression technology, in view of the problems existing in the previous technology. The present invention can be migrated to other multi-channel signal acquisition circuits.

To tackle the area and power consumption challenges in the existing technology mentioned in the background, the present invention applies frequency division multiplexing technology to the data compression block of the electrical impedance tomography chip to achieve both lower area and power consumption. Frequency division multiplexing technology modulates narrow-bandwidth signals from different channels into different frequencies and further combines them into a wide-bandwidth signal, so that multiple channel signals can be processed by a single circuit module. It can help substantially reduce hardware overhead; and at the same time, cut down the power consumption of each channel. On-chip data compression can also be realized taking advantage of the frequency division multiplexing process.

These features mentioned above can be strong evidence that the present invention, especially frequency division multiplexing technology, is an effective design scheme for multi-channel narrow bandwidth bio-signal acquisition circuits.

To achieve the above object, the technical solution of the present invention is as follows.

The present invention provides an electrical impedance tomography system with frequency division multiplexing based data compression, and the system comprises electrodes, a connecting line, an electrical impedance tomography chip, a universal serial bus (USB) and a computer. The system is characterized in that the electrodes comprise M identical discrete electrodes, wherein M is a positive integer above 2.

In the present invention, the electrical impedance tomography chip comprises a clock generator, a current stimulator, the electrode control block, the analog front-end signal acquisition block, and the data compression and sampling block.

In the present invention, the clock generator is connected to the clock input end of the current stimulator, the electrode control block, the analog front-end signal acquisition block and the data compression and sampling block at the output end. The clock generator is used to generate the clock signals required for each part of the chip.

In the present invention, the output end of the current stimulator is connected to the M electrodes respectively via the electrode control block. The electrode control block switches the electrodes between the two modes: current injection or signal acquisition. The electrode control block supplies the current generated by the current stimulator to the electrodes which are in the current injection mode to inject a safe-intensity current of certain frequency to the human body; in the meantime, acquires voltage signals from the electrodes which are in the signal acquisition mode and transmits them to the analog front-end signal acquisition block.

In the present invention, the analog front-end signal acquisition block comprises analog front-end signal acquisition circuits of M−3 channels, that is, the first channel analog front-end signal acquisition circuit, . . . , the seventh channel analog front-end signal acquisition circuit, . . . , the $(M-3)^{th}$ channel analog front-end signal acquisition circuit. The analog front-end signal acquisition circuit of each channel includes two outputs, making a total of 2(M−3) outputs.

In the present invention, the data compression and sampling block comprises 2(M−3) choppers, two adders, two delta-sigma modulators (DSM).

In the present invention, the 2(M−3) outputs of the (M−3)—channel analog front-end signal acquisition block are respectively connected to the input terminals of the 2(M−3) choppers, and the 2(M−3) choppers shifts the received signals to M−3 different frequency bands $f_{c,2}, \ldots, f_{c,M-3}$. The output signals of the output of the 2(M−3) choppers are divided into two groups, respectively entering adder one and adder two. Adder one and adder two are configured to combine the collected signals into two data streams for quantization, realizing frequency division multiplexing based data compression.

In the present invention, the delta-sigma modulators include delta-sigma modulator one and delta-sigma modulator two. The input of delta-sigma modulator one is connected to the output of adder one; the input of delta-sigma modulator two is connected to the output of adder two. The delta-sigma modulators quantize the data stream obtained by the adder, and then transfer it to the computer through the universal serial bus. The computer mentioned is in charge of the subsequent data processing and imaging.

The electrical impedance tomography chip of the present invention can be made into a printed circuit board (PCB).

The present invention further provides an imaging method for electrical impedance tomography using the electrical impedance tomography system with frequency division multiplexing (FDM) based data compression comprising the following steps:

(1) Place the electrodes around the thoracic cavity of the subject, connecting all the components properly.

(2) When the measurement is started, under the control of the electrode control block, the electrodes rotate between states described below:

State 1: the adjacent electrodes $E_1$ and $E_2$ are set to current injection mode; at the same time, the other electrodes are set to signal acquisition mode; read the voltage signals reflected by the M−3 pairs of adjacent electrodes in signal acquisition mode, that is, $E_3$ and $E_4$, $E_4$ and $E_5$, ..., $E_{M-1}$ and $E_M$; data collected flows through the analog front-end signal acquisition block, the data compression and sampling block and finally to the computer;

State 2: the adjacent electrodes $E_2$ and $E_3$ are set to current injection mode; at the same time, the other electrodes are set to signal acquisition mode; read the voltage signals reflected by the M−3 pairs of adjacent electrodes in signal acquisition mode, that is, $E_4$ and $E_5$, $E_5$ and $E_6$, ..., $E_M$ and $E_1$; data collected flows through the analog front-end signal acquisition block, the data compression and sampling block and finally to the computer; . . . .

State M: the adjacent electrodes $E_M$ and $E_1$ are set to current injection mode; at the same time, the other electrodes are set to signal acquisition mode; read the voltage signals reflected by the M−3 pairs of adjacent electrodes in signal acquisition mode, that is, $E_2$ and $E_3$, $E_3$ and $E_4$, ..., $E_{M-2}$ and $E_{M-1}$; data collected flows through the analog front-end signal acquisition block, the data compression and sampling block and finally to the computer.

(3) After a complete rotation cycle, the present computer restores one frame of image by post-processing of the voltage signal information collected during the whole cycle, more specifically, by algorithm software to reconstruct and display the electrical impedance image.

In the present invention, the electrical impedance tomography chip (4), as a system on chip (SoC), includes the main functional modules of the electrical impedance tomography system with frequency division multiplexing based data compression in the present invention, which concentratedly embodies the application of frequency division multiplexing technology in the present invention.

In the present invention, the computer is used for data processing and image restoration.

The benefits of the present invention are as follows:

Compared with conventional electrical impedance tomography systems, the present invention combines frequency division multiplexing technology to modulate narrow-bandwidth signals from different channels into different frequencies and further combines them into a wide-bandwidth signal, so that multiple channel signals can be processed by a single circuit module. It can help substantially reduce hardware overhead; and at the same time, cut down the power consumption of each channel. On-chip data compression can also be realized taking advantage of the frequency division multiplexing process.

Compared with conventional electrical impedance tomography systems which apply time division multiplexing technology, frequency division multiplexing technology implemented in the present invention is more advantageous for data compression and fusion. It achieves that the data stream of each frame of the image generated by the electrical impedance tomography chip contains only two M-bit outputs.

BRIEF DESCRIPTION OF THE DRAWINGS

FIGS. 6A to 6D show the test model used by the embodiment of the present invention and images restored by the proposed pulmonary monitoring electrical impedance tomography system with frequency division multiplexing based data compression, among which, FIG. 6A shows the water tank with two plastic cylinders 8 and 9 in the first case; FIG. 6B shows the restored image of the water tank with the cylinders of FIG. 6A by the system of the present invention; FIG. 6C shows the water tank 7 with one plastic cylinder 10 and one metal cylinder 11 in the second case; and FIG. 6D shows the restored image of the water tank with the cylinders of FIG. 6C by the system of the present invention.

DETAILED DESCRIPTION OF THE INVENTION

The present invention is further described with reference to the following embodiment, taken in conjunction with the accompanying drawings, which should not be taken to limit the scope of the invention.

Figure 1:
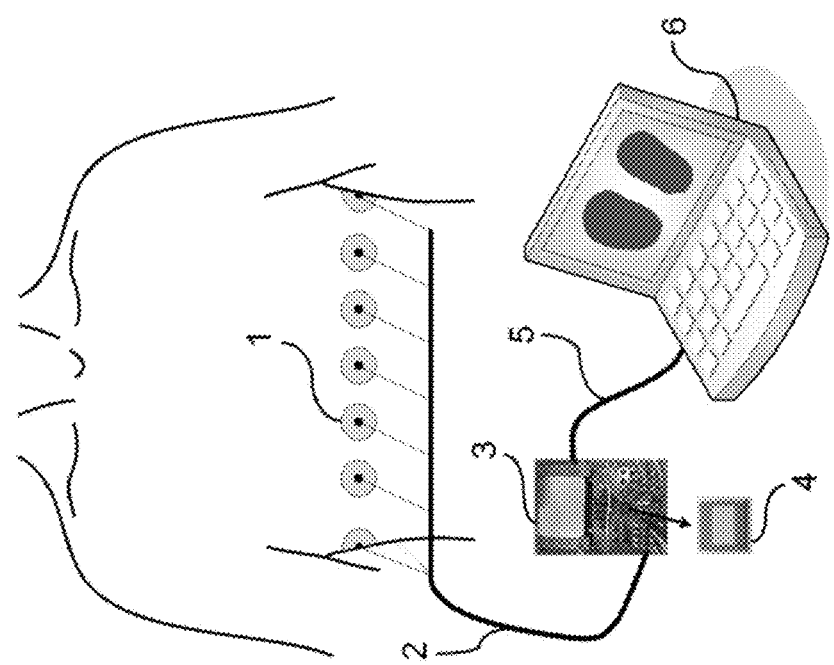
FIG. 1 shows the hardware connection of the proposed pulmonary monitoring electrical impedance tomography system with frequency division multiplexing based data compression according to the present invention.

FIG. 1 shows the hardware connection of the proposed pulmonary monitoring electrical impedance tomography system with frequency division multiplexing based data compression according to the present invention.

Figure 2:
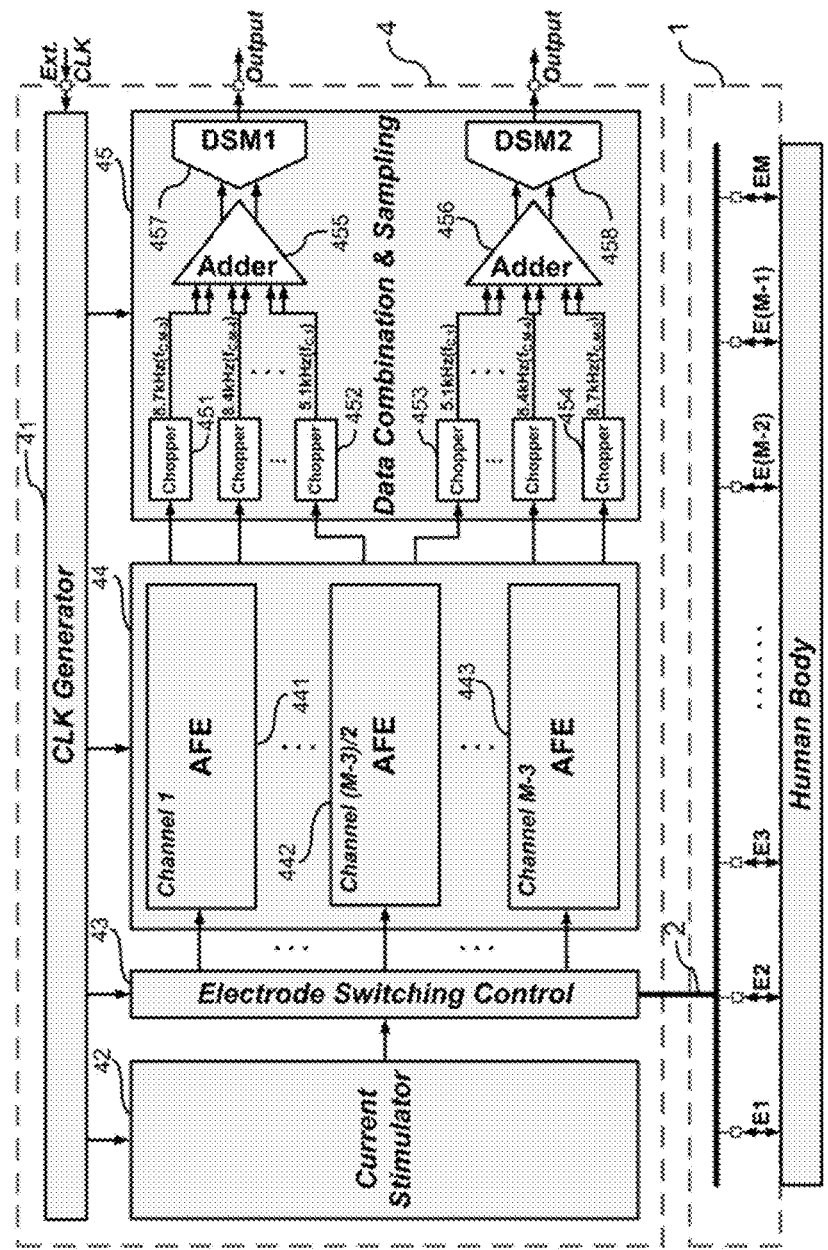
FIG. 2 shows schematic diagram of the circuit structure of the electrical impedance tomography chip (4) in the present invention.

FIG. 2 shows schematic diagram of the circuit structure of the electrical impedance tomography chip (4) in the present invention. In this embodiment, M=16.

As FIG. 1 shows, the electrical impedance tomography system with frequency division multiplexing based data compression in this embodiment of the present invention comprises: electrodes 1, connecting line 2, printed circuit board 3, electrical impedance tomography chip 4, universal serial bus 5 and computer 6.

Electrodes 1 comprises sixteen identical electrodes: $E_1$, $E_2$, $E_3$, $E_4$, $E_5$, $E_6$, $E_7$, $E_8$, $E_9$, $E_{10}$, $E_{11}$, $E_{12}$, $E_{13}$, $E_{14}$, $E_{15}$, $E_{16}$. For better contact, lower noise and better signal quality, electrodes 1 adopt wet electrodes.

Printed circuit board 3 includes peripheral circuits such as gain configuration circuit for the programmable gain amplifiers.

Figure 4:
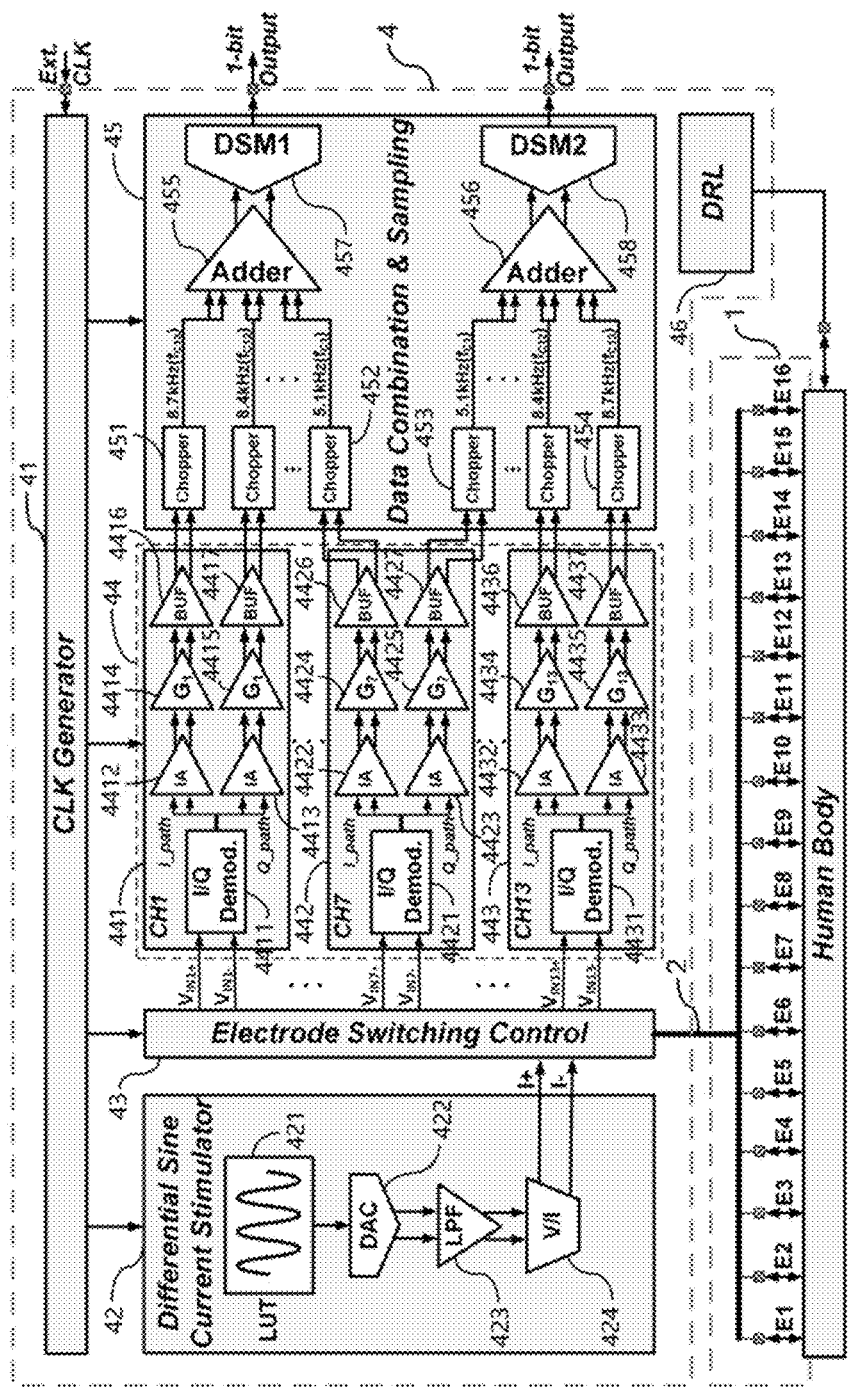
FIG. 4 shows schematic diagram of the circuit structure implemented by electrical impedance tomography imaging chip (4) according to the embodiment of the present invention.

Turning to electrical impedance tomography chip 4, the specific system architecture is as shown in FIG. 4, and includes: clock generator 41, current stimulator 42, electrode control block 43, analog front-end signal acquisition block 44, the data compression and sampling block 45 and driven right leg (DRL) block 46.

Clock generator 41 is connected to the clock input end of current stimulator 42, electrode control block 43, analog front-end signal acquisition block 44 and data compression and sampling block 45 at the output end. The clock generator is used to generate the clock signals required for each part of the chip.

Current stimulator 42 generates a safe-intensity current and injects it to the subject (human body) via electrodes 1, comprising: Look up table (LUT) 421, digital analog converter (DAC) 422, low pass filter (LPF) 423, and voltage to current converter 424.

Figure 3:
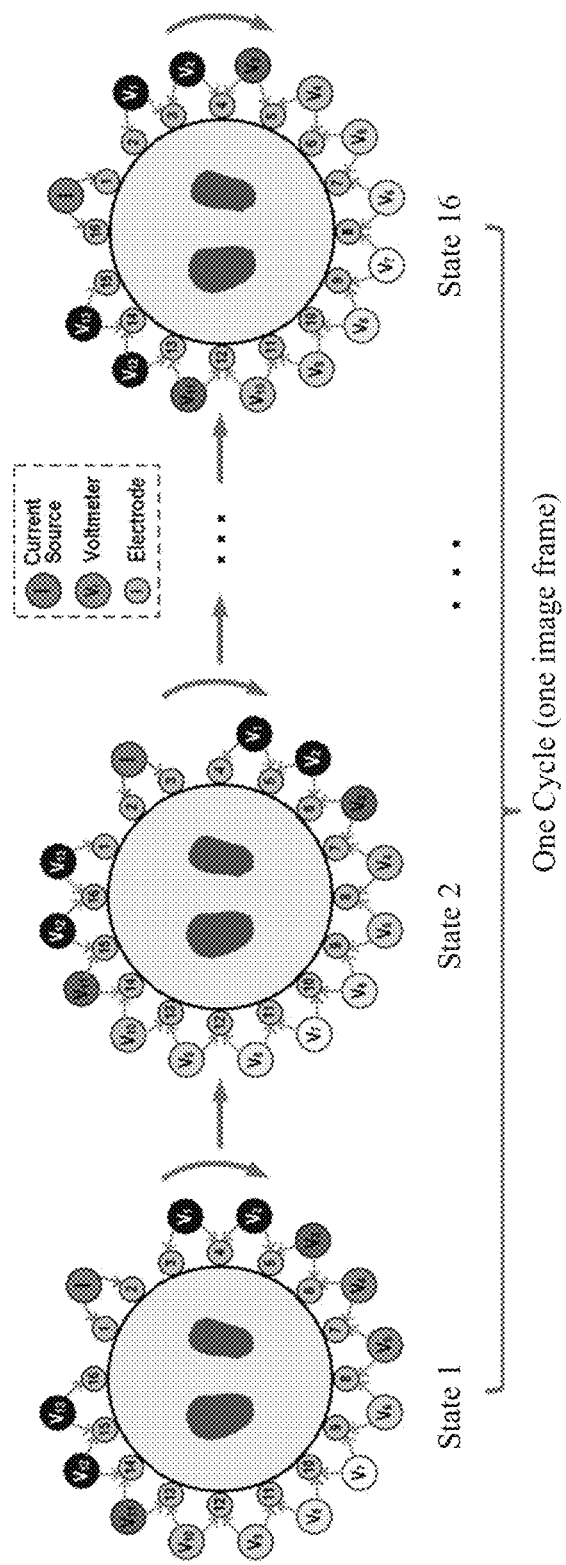
FIG. 3 shows the state of the electrodes' switch throughout a complete rotation cycle (i.e., generating one frame of image) according to the present invention.

Electrode control block 43 switches the electrodes between the two modes: current injection or signal acquisition. FIG. 3 shows the state of the electrodes' switch throughout a complete rotation cycle (i.e., generating one frame of image) according to the present invention. Electrode control block 43 supplies the current generated by current stimulator 42 to the electrodes which are in the current injection mode to inject current of certain frequency to the human body; in the meantime, acquires voltage signals from the electrodes which are in the signal acquisition mode and transmits them to the analog front-end signal acquisition block.

Analog front-end signal acquisition block 44 comprises: analog front-end signal acquisition circuits of M−3 channels, that is, the first channel analog front-end signal acquisition circuit 441, ..., the seventh channel analog front-end signal acquisition circuit 442, ..., the $(M-3)^{th}$ channel analog front-end signal acquisition circuit 443. Take the first channel analog front-end signal acquisition circuit 441 as an example, analog front-end signal acquisition circuit for each channel comprises:

I/Q demodulation circuit 4411, instrumentation amplifier (IA) 4412 and 4413, programmable gain amplifier (PGA) 4414 and 4415, and buffer 4416 and 4417. Among them, I/Q demodulation circuit 4411 has outputs divided into two paths, one of which in sequence flows to instrumentation amplifier 4412, programmable gain amplifier 4414 and buffer 4416, and the other in sequence flows to instrumentation amplifier 4413, programmable gain amplifier 4415 and buffer 4617.

Data compression and sampling block 45 comprises: chopper 451 to 454 (26 choppers in total), adder 455 and 456, delta-sigma modulator 457 and 458, wherein:

A total of 26 choppers (451 to 454) respectively shift the received signals to 13 different frequency bands $f_{c,2}$, ..., $f_{c,13}$. The output signals of the output of the 26 choppers are divided into two groups, respectively flowing into adder 455 and 456.

Adder 455 and adder 456 are configured to combine the collected signals into two data streams for quantization, realizing frequency division multiplexing based data compression.

Delta-sigma modulator 457 and 458 quantize the data stream obtained by adder 455 and 456, and then transfer it to computer 6 through universal serial bus 5.

Driven right leg block 46 helps to stabilize common mode voltage and improve noise performance.

Computer 6 is in charge of the data processing and imaging.

When the power is on and measurement is started, current stimulator 42 on electrical impedance tomography chip 4 injects current of certain frequency to the subject (human body) via one pair of electrodes, and voltage signals are captured at other electrodes. FIG. 3 can be referred to. Under the control of electrode control block 43, electrodes 1 are had to rotate between 16 states described below:

State 1: the adjacent electrodes $E_1$ and $E_2$ are set to current injection mode; At the same time, the other electrodes are set to signal acquisition mode. Voltage signals reflected by the 13 pairs of adjacent electrodes in signal acquisition mode, that is, $E_3$ and $E_4$, $E_4$ and $E_5$, ..., $E_{15}$ and $E_{16}$ are read.

State 2: the adjacent electrodes $E_2$ and $E_3$ are set to current injection mode; At the same time, the other electrodes are set to signal acquisition mode. Voltage signals reflected by the 13 pairs of adjacent electrodes in signal acquisition mode, that is, $E_4$ and $E_5$, $E_5$ and $E_6$, ..., $E_{16}$ and $E_1$ are read.

. . .

State 16: the adjacent electrodes $E_{16}$ and $E_1$ are set to current injection mode; At the same time, the other electrodes are set to signal acquisition mode. Voltage signals reflected by the 13 pairs of adjacent electrodes in signal acquisition mode, that is, $E_2$ and $E_3$, $E_3$ and $E_4$, ..., $E_{14}$ and $E_{15}$ are read.

Data collected flows through analog front-end signal acquisition block 44, the data compression and sampling block 45 and finally to computer 6 through universal serial bus 5. After a complete rotation cycle, computer 6 restores one frame of image by post-processing of the voltage signal information collected during the whole cycle, more specifically, by EIDORS (Electrical Impedance Tomography and Diffuse Optical Tomography Reconstruction Software).

Figure 5:
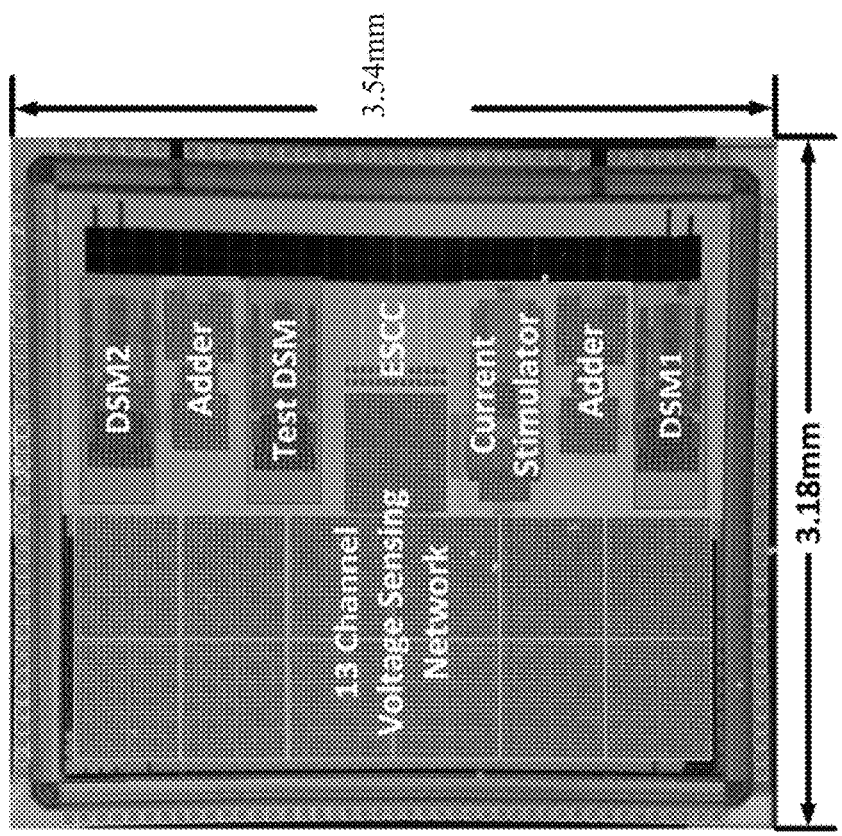
FIG. 5 shows the circuit block layout of the electrical impedance tomography chip (4) demonstrated in FIG. 4 according to the embodiment of the present invention.

Electrical impedance tomography chip 4 has taped out using CMOS 0.13 micrometer process. The power consumption per channel turns out to be 118 microwatts and the area is 0.87 square millimeters, verifying the effectiveness of the present invention. FIG. 5 shows the circuit block layout of electrical impedance tomography chip 4.

Figures 6A, 6B, 6C, 6D:
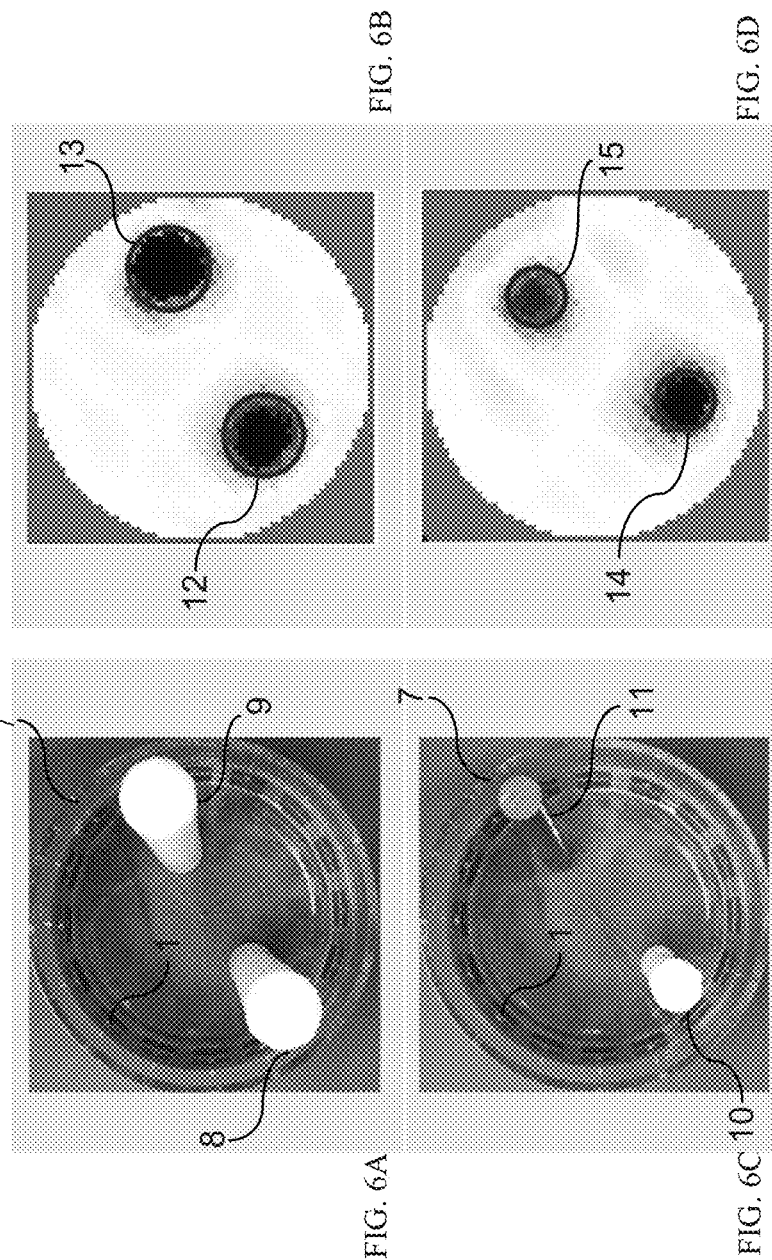

FIGS. 6A to 6D show the test model used by the embodiment of the present invention and images restored by the proposed pulmonary monitoring electrical impedance tomography system with frequency division multiplexing based data compression. When testing, water tank 7 with cylinders made of different material is used to model the shape of lung. Electrodes 1 are attached to the inner side wall of water tank 7. In the first case as shown in FIG. 6A, water tank 7 has two plastic cylinders in it, referred to as plastic cylinder 8 and plastic cylinder 9. With the present system in this embodiment, the restored image on the right side as shown in FIG. 6B is obtained. There is blue region 12 and blue region 13 in the restored image in FIG. 6B, respectively showing the position, size, and general shape of the two plastic cylinders. In the second case as shown in FIG. 6C, water tank 7 has one plastic cylinder 10 and one metal cylinder 11 in it. With the present system in this embodiment, the restored image on the right side as shown in FIG. 6D is obtained. There is blue region 14 showing the position, size, and general shape of plastic cylinder 10 and red region 15 showing the position, size, and general shape of the metal cylinder 11 in the restored image in FIG. 6D. It should be noted that in the restored image, such as FIGS. 6B and 6D, the blue mark indicates that the conductivity is low, the red mark indicates that the conductivity is high, and the color brightness indicates the measured relative conductivity.

It should be noted that, to describe the present invention more simply, electrical impedance tomography system for pulmonary monitoring is taken as an example in this embodiment, but the pulmonary monitoring herein may be application in any other field. In this case, the system is still under the protection scope of the present patent for there is no creative labor.

It should be noted that, to describe the present invention more simply, a 16-electrode system is taken as an example in this embodiment, but the electrode quantity 16 herein may be changed into any other. In this case, the system is still under the protection scope of the present patent for there is no creative labor.

Figure 7:
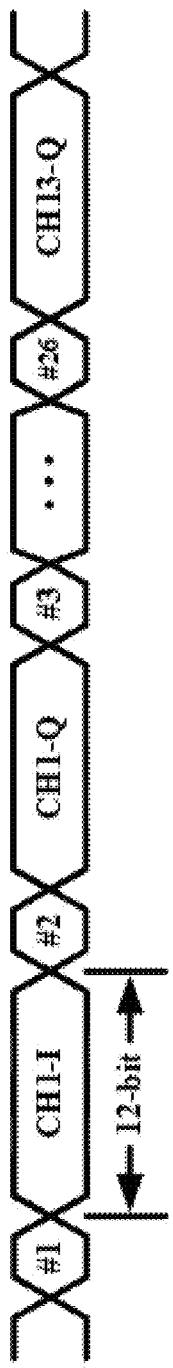
FIG. 7 shows a data flow diagram of a pulmonary monitoring electrical impedance tomography system employing time division multiplexing technique in existing technology.
Figure 8:
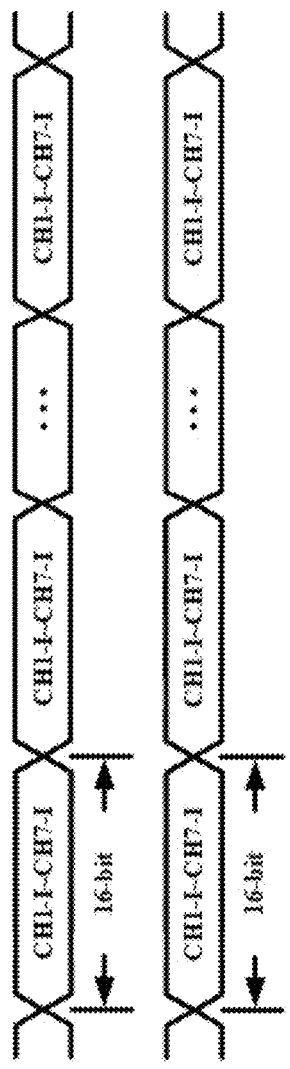
FIG. 8 shows the data flow diagram of the pulmonary monitoring electrical impedance tomography system with frequency division multiplexing based data compression according to the embodiment of the present invention.

On-chip 13-channel data combination is obtained thanks to the frequency division multiplexing technique. This is best illustrated in the data stream of the conventional time division multiplexing scheme shown in FIG. 7 and the proposed frequency division multiplexing scheme shown in FIG. 8. There are 26 12-bit output per reading for time division multiplexing system. In the proposed system, two capacitive-coupled adders are used to assemble the 26 I/Q signals into two groups. Channel 1-I, 1-Q, . . . , 6-Q, and 7-I are combined into the first frequency division multiplexing signal, while channel 7-Q, 8-I, . . . , 13-I, and 13-Q are combined into the second frequency division multiplexing signal for symmetric reason of the amplitudes. Two 16-bit resolution DSMs are used to quantize the two assembled 13 I/Q components as: $13 \times 2^{12} = 2^{15.7} < 2^{16}$, resulting in only two 16-bit output per reading.

It turns out that the embodiment of the present invention provides an electrical impedance tomography chip that reduces the power consumption per channel to 118 microwatts, and the area to 0.87 square millimeters. Finally, the electrical impedance tomography imaging chip in the embodiment of the present invention can generate a pulmonary electrical impedance tomographic image of 5 frames per second.

We claim:

1. An electrical impedance tomography system with frequency division multiplexing based data compression, comprising
electrodes (1),
a connecting line (2),
an electrical impedance tomography chip (4),
a universal serial bus (USB) (5), and
a computer (6),
wherein the electrodes (1) comprise M number of identical discrete electrodes $E_1, E_2, \ldots E_{M-1}, E_M$), M is a positive integer that is more than 2,
the electrical impedance tomography chip (4) comprises a clock generator (41) having an output end, a current stimulator (42) having a clock input end and an output end, an electrode control block (43) having a clock input end, an analog front-end signal acquisition block (44) having a clock input end, and a data compression and sampling block (45) having a clock input end, the output end of the clock generator (41) is connected to the clock input ends of the current stimulator (42), the electrode control block (43), the analog front-end signal acquisition block (44), and the data compression and sampling block (45) for generating clock signals required for each part of the chip, the output end of the current stimulator (42) is connected to one end of the M numbers of the electrodes (1), respectively, via the electrode control block (43), the electrode control block (43) switches the electrodes (1) between a current injection mode and a signal acquisition mode, supplies current generated by the current stimulator (42) to the electrodes (1) that are in the current injection mode to inject a current having a frequency safe for a human body and in the meantime, acquires voltage signals from the electrodes (1) that are in the signal acquisition mode, and transmits the acquired voltage signals from the electrodes (1) to the analog front-end signal acquisition block (44), the analog front-end signal acquisition block (44) comprises analog front-end signal acquisition circuits having (M-3) numbers of channels being a first channel analog front-end signal acquisition circuit, a second channel analog front-end signal acquisition circuit, . . . , a seventh channel analog front-end signal acquisition circuit, . . . , and up to a (M-3)$^{th}$ channel analog front-end signal acquisition circuit, and the analog front-end signal acquisition circuit of each channel comprises two output ends so that a total number of output ends is 2(M-3), and the data compression and sampling block (45) comprises 2(M-3) numbers of choppers, each having an input terminal and output end, a first adder and a second adder, each having an output end, and a first delta-sigma modulator and a second delta-sigma modulator, each having an input end, wherein the 2(M-3) numbers of the outputs of the (M-3)—channel analog front-end signal acquisition block are respectively connected to the input terminals of the 2(M-3) choppers, the 2(M-3) numbers of the choppers shifts signals received to M-3 different frequency bands $f_{c,2}, \ldots, f_{c,M-3}$, output signals of the output ends of the 2(M-3) numbers of the choppers are divided into a first group and a second group, and the two groups of the output signals enter the first adder and the second adder, respectively, and the first adder and the second adder are configured to combine collected signals into two data streams for quantization to realize frequency division multiplexing based data compression.

2. The system of claim 1, wherein the input end of the first delta-sigma modulator is connected to the output end of the first adder,
the input end of the second delta-sigma modulator is connected to the output end of the second adder,
the first and second delta-sigma modulators quantize data stream obtained by the adders, and transfer the data stream to the computer (6) through the universal serial bus (5), and
the computer (6) conducts data processing and imaging.

3. The system of claim 1, wherein the electrical impedance tomography chip (4) is a printed circuit board (PCB).

* * * * *